United States Patent [19]
Hagan et al.

[11] 3,973,002
[45] Aug. 3, 1976

[54] ANTIHEMOPHILIC FACTOR
[75] Inventors: James J. Hagan, Holmdel; Charles Glaser, Raritan, both of N.J.
[73] Assignee: E. R. Squibb & Sons, Inc., Princeton, N.J.
[22] Filed: May 1, 1975
[21] Appl. No.: 573,684

Related U.S. Application Data
[63] Continuation-in-part of Ser. No. 460,417, April 12, 1974, abandoned.

[52] U.S. Cl. .......................... 424/101; 260/112 B; 424/177
[51] Int. Cl.² ................. A61K 35/14; C07G 7/026
[58] Field of Search ........................ 424/101, 177; 260/112 B

[56] References Cited
UNITED STATES PATENTS
3,803,115   4/1974   Fekete et al. .................. 260/112 B OTHER PUBLICATIONS
Newman et al., British Journal of Haematology, 1971, 21, pp. 1-20.
Johnson et al., British Journal of Haematology, 1971, 21, pp. 21-41.
Weiss et al., British Journal of Haematology, 1970, 18, pp. 89-100.

Primary Examiner—Donald B. Moyer
Attorney, Agent, or Firm—Lawrence S. Levinson; Merle J. Smith; Burton Rodney

[57] ABSTRACT
A quick-dissolving antihemophilic factor preparation is obtained by adjusting the pH of buffer-extracted plasma cryoprecipitate to from about pH 6 to about pH 7.0 and cooling to a temperature of from about 2°C to about 20°C for from about 15 minutes to about 1 hour, in order to precipitate certain protein impurities, primarily fibrinogen.

10 Claims, No Drawings

ANTIHEMOPHILIC FACTOR

REFERENCE TO OTHER APPLICATIONS

This application is a continuation-in-part of application Ser. No. 460,417, Apr. 12, 1974 now abandoned.

BACKGROUND OF THE INVENTION

The isolation of the antihemophilic factor (hereafter called AHF) from blood plasma has been of enormous benefit to hemophiliacs. It enables them to control their bleeding and to lead a near normal life. A disadvantage of the present AHF, however, is its slow dissolution when being reconstituted for use.

OBJECTS OF THE INVENTION

It is, accordingly, an object of the present invention to provide an improved AHF. Another object is to provide an AHF having increased purity over current low purity preparations. A further object is to provide an AHF having faster dissolution properties. These and other objects of the present invention will be apparent from the following description.

SUMMARY OF THE INVENTION

It has now been found that an improved, purer, quicker-dissolving AHF is obtained by adjusting the pH of buffer-extracted plasma cryoprecipitate to a pH in the range of from about pH 6 to about pH 7.0, and cooling to a temperature of from about 2°C to about 20°C for from about 15 minutes to about 1 hour in order to precipitate protein impurities.

DETAILED DESCRIPTION

The starting material for obtaining AHF is fresh frozen human blood plasma. The fresh frozen plasma is thawed under controlled conditions such that the temperature of the plasma never exceeds about 1°C during the entire thawing operation. The thawed plasma is filtered and centrifuged at about 0°C to remove a cryoprecipitate. The cryoprecipitate is macerated, stirred in a buffer such as tris hydrochloride or tris sulfate solution or a citrate dextrose buffer solution having a pH of from about 7.0 to about 7.5 and centrifuged. The pH of the supernatant liquor is then adjusted to a pH of from about 7.0 to about 7.5 and filtered. The filtrate is then optionally stirred with an aluminum hydroxide slurry at 18° to 25°C using a volume containing 82 to 90 mg of $Al_2O_3$ for each liter of starting plasma. The suspended solid is removed by centrifugation at 18° to 25°C.

The supernatant solution is adjusted to a pH of from about 6 to about 7.0 and preferably from about 6.2 to about 6.6 with mineral acid. The supernatant is then quickly cooled to from about 2°C to about 20°C, and preferably 15°C, and held at this temperature to precipitate an inert fibrous solid, namely fibrinogen. Generally, a period of up to about 1 hour is required to precipitate the solid. The suspension is filtered and the supernate clarified by high speed centrifugation while maintaining the temperature constant in the range of from about 2° to 20°C. The precipitation of impurities is a function of the temperature and pH. The lower temperatures are employed with the higher pH values, while higher temperatures may be employed with lower pH values. The pH of the solution is then adjusted to from about 7.0 to about 7.5 with 1 N NaOH or $NH_4OH$, or 1M tris(hydroxymethyl)amino methane HCl, and, if not absolutely clear, the solution is further clarified by filtration. The solution is then stabilized by adding 0.5 M sodium citrate to give a final concentration of about 0.02 M sodium citrate. If millipore filtration is not required for clarification, the solution is then sterilized by filtration and filled into suitable size graduated bottles in a sterile room using aseptic techniques. Each bottle contains at least 250 AHF units. The bottles are then lyophilized. Upon reconstitution with sterile water for injection, the AHF dissolves completely in less than 5 minutes, generally in less than 3 minutes. By way of contrast, prior art techniques which employ aluminum oxide treatment and do not include the low temperature-low pH step yield an AHF which often requires 20 minutes or more to dissolve, and which sometimes fails to dissolve completely even on prolonged standing.

The following examples illustrate preferred embodiments of the present invention without, however, limiting the same thereto.

EXAMPLE 1

1. Fresh frozen human plasma (300 liters) is placed in stainless steel trays and allowed to remain at 2°–6°C until partially thawed. The soft cakes of plasma are then transferred to a 400 liter jacketed stainless steel tank and thawed by circulating water at 30° through the jacket while gently stirring. The temperature of the plasma is not permitted to exceed 1°C during the entire thawing operation.

2. The thawed plasma is filtered through a stainless steel screen (with 3mm circular openings) into a stainless steel pressure tank and immediately transferred to the −5°C room. The filtered plasma is centrifuged at 0°±1°C at an approximate rate of 30 to 50 liters per hour to remove the cryoprecipitate.

3. The cryoprecipitate is macerated, suspended in 9 liters of citrate-dextrose buffer, pH 7, and stirred gently at 18°C to 25°C. The solution is centrifuged and the precipitate discarded.

4. The buffer extract is adjusted to pH 6.3 with 1 N hydrochloric acid and cooled quickly to 15°±1°C. The extract is held at this temperature for 30 minutes in order to precipitate an inert fibrous solid. The precipitate is removed by passing the extract through cheesecloth or nylon and then clarified by high speed centrifugation at a temperature which will maintain the solution at 15°±1°C. Tris(hydroxymethyl) amino methane is added to a concentration of 0.02M. The solution is quickly adjusted to pH 7.1±0.1 with 1 N sodium hydroxide and, if not absolutely clear, further clarified by passing the solution through a Millipore or Cox Membrane.

5. The clarified extract is sterilized by filtration, collected in a sterile bottle, and then filled in a sterile room using aseptic techniques into suitable size graduated bottles calculated to contain at least 250 AHF units.

6. The filled bottles are immediately stoppered and shell frozen in a dry ice, alcohol bath. Using sterile technique, the stoppers of the frozen bottles are retracted to the drying position, placed in covered trays and wrapped with 5% phenol-soaked cheesecloth. The trays are stored at −30°C until lyophilization is complete.

7. The lyophilized product is reconstituted for use by addition of 25 ml of sterile water for injection, U.S.P. Complete dissolution is obtained in 1.5 minutes.

EXAMPLE A (COMPARATIVE)

The foregoing procedure is repeated except that the following procedures are employed in lieu of steps 3, 4 and 7:

3. The cryoprecipitate is macerated, suspended in 9 liters of tris (hydroxymethyl)amine methane hydrochloride (tris buffer), pH 7.0, and stirred gently at 18°–25°C. The solution is centrifuged and the precipitate discarded.

4. The buffer extract is adjusted to pH 7.0, if necessary. The extract is stirred for 3 minutes with an aluminum oxide slurry using a volume containing 25.8 g of aluminum oxide. The extract is clarified by centrifugation and the solution is adjusted to pH 7.1±0.1 with sodium citrate buffer to give a final concentration of 0.02 molar sodium citrate. The solution is then sterilized by passing through a Millipore membrane.

7. The lyophilized product is reconstituted for use by addition of 25 ml of sterile water for injection, U.S.P. Complete dissolution does not occur until after 10 minutes.

EXAMPLE 2

1. Fresh frozen human plasma (300 liters) are placed in stainless steel trays and allowed to remain at 2°–6°C until partially thawed. The soft cakes of plasma are then transferred to a 400 liter jacketed stainless steel tank and thawed by circulating water at 30° through the jacket while gently stirring. The temperature of the plasma is not permitted to exceed 1°C during the entire thawing operation.

2. The thawed plasma is filtered through a stainless steel screen (with 3mm circular openings) into a stainless steel pressure tank and immediately transferred to the −5°C room. The filtered plasma is centifuged at 0°±1°C at an approximate rate of 30 to 50 liters per hour to remove the cryoprecipitate.

3. The cryoprecipitate is macerated, suspended in 9 liters of tris(hydroxymethyl)amino methane hydrochloride buffer, pH 7, and stirred gently at 18°C to 25°C. The solution is centrifuged and the precipitate discarded.

4. The buffer extract is adjusted to pH 7.0, if necessary. The extract is stirred for 3 minutes with an aluminum oxide slurry using a volume containing 86 mg aluminum oxide for each liter of starting plasma.

5. The buffer extract is adjusted to pH 6.4±0.2 with 1N hydrochloric acid and cooled quickly to 15°±1°C. The extract is held at this temperature for 30 minutes in order to precipitate an inert fibrous solid. The precipitate is removed by passing the extract through cheesecloth or nylon and then clarified by high speed centrifugation at a temperature which will maintain the solution at 15°C±1°C. Tris(hydroxymethyl)amino methane hydrochloride is added to adjust the solution to pH 7.

6. The extract is stabilized with sodium citrate buffer to give a final concentration of 0.02 molar sodium citrate. If the solution is not absolutely clear, it is clarified by passing the solution through a Millipore or Cox Membrane.

7. The clarified extract is sterilized by filtration, collected in a sterile bottle, and then filled in a sterile room using aseptic techniques into suitable size graduated bottles calculated to contain at least 250 AHF units.

8. The filled bottles are immediately stoppered and shell-frozen. Using sterile technique, the stoppers of the frozen bottles are retracted to the drying position, placed in covered trays and wrapped with 5% phenol-soaked cheesecloth. The trays are stored at −30°C until lyophilization is complete.

9. The lyophilized product is reconstituted for use by addition of 25 ml of sterile water for injection, U.S.P. Complete dissolution is obtained in 1.5 minutes.

What is claimed is:

1. In a method for isolating antihemophilic factor of human blood plasma, the improvement comprising adjusting the pH of a solution of buffer-extracted plasma cryoprecipitate to from about 6.0 to about 7.0, and cooling the solution at a temperature of from about 2°C to about 20°C for from about 15 to about 60 minutes to cause precipitation of impurities.

2. A method according to claim 1 wherein the solution is held at a temperature of about 15°C and the resulting precipitated impurities are removed.

3. In a method for preparing lyophilized antihemophilic factor of human blood plasma wherein thawed frozen human blood plasma is centrifuged at a temperature of about 0°C to remove a cryoprecipitate, the cryoprecipitate is macerated, the macerated cryoprecipitate is extracted with buffer, the suspension is centifuged and the precipitate is discarded to obtain a buffer extract, the pH of the extract is adjusted to about 7.0–7.2 and the extract is sterilized and lyophilized, the improvement comprising adjusting the pH of the buffer extract to from about pH 6.0 to about pH 7.0, and cooling to a temperature of from about 2°C to about 20°C to precipitate an inert fibrous solid, and removing the precipitate while maintaining the temperature of the extract at a temperature of from about 2°C to about 20°C.

4. A method according to claim 3 wherein the buffer extract is cooled to a temperature of about 15°C and the precipitated impurity is removed.

5. A method according to claim 3 wherein said buffer comprises Tris hydrochloride or sulfate.

6. A method according to claim 3 wherein said buffer comprises a citrate-dextrose buffer.

7. A method according to claim 3 further including the step of mixing the buffer extract, prior to adjusting the pH thereof to 6 – 7, with aluminum hydroxide slurry.

8. A method according to claim 7 further including the improvement of adding sodium citrate to the buffer extract after adjusting the pH thereof to between 6 and 7, and then about neutral to stabilize said buffer extract.

9. A lyophilized antihemophilic factor of human blood plasma prepared according to the method of claim 3.

10. A lyophilized antihemophilic factor of human blood plasma prepared according to the method of claim 8.

* * * * *